(12) United States Patent
Koslow et al.

(10) Patent No.: US 6,355,330 B1
(45) Date of Patent: Mar. 12, 2002

(54) CONTINUOUS SOLID STATE WEB COATING PROCESS AND WEBS PRODUCED THEREBY

(75) Inventors: Evan E. Koslow, Weston; Richard D. Kendrick, Stratford; Gordon Spilkin, Stamford, all of CT (US)

(73) Assignee: Koslow Technologies Corporation, Orange, CT (US)

( * ) Notice: Subject to any disclaimer, the term of this patent is extended or adjusted under 35 U.S.C. 154(b) by 0 days.

(21) Appl. No.: 09/358,183

(22) Filed: Jul. 20, 1999

Related U.S. Application Data

(60) Continuation-in-part of application No. 08/903,395, filed on Jul. 22, 1997, now Pat. No. 6,077,588, which is a division of application No. 08/813,055, filed on Mar. 7, 1997, now Pat. No. 5,792,513.

(51) Int. Cl.[7] .................................................. B32B 5/12
(52) U.S. Cl. ..................... 428/114; 604/355; 604/356; 604/358; 604/359; 604/360; 604/366
(58) Field of Search .......................... 428/114; 604/355, 604/356, 358, 259, 360, 366

(56) References Cited

U.S. PATENT DOCUMENTS

| | | | |
|---|---|---|---|
| 4,055,184 A | * 10/1977 | Karami | 128/287 |
| 4,420,590 A | 12/1983 | Gartner | 525/357 |
| 4,626,252 A | * 12/1986 | Nishizawa et al. | 604/370 |
| 5,147,722 A | 9/1992 | Koslow | 428/402 |
| 5,151,301 A | 9/1992 | Kruger et al. | 427/294 |
| 5,225,242 A | 7/1993 | Frankosky et al. | 427/209 |
| 5,328,450 A | * 7/1994 | Smith et al. | 602/59 |
| 5,360,419 A | 11/1994 | Chen et al. | 604/374 |
| 5,413,747 A | 5/1995 | Akers et al. | 264/211 |
| 5,462,538 A | * 10/1995 | Korpman | 604/372 |
| H1732 H | * 6/1998 | Johnson | 428/68 |
| 5,861,144 A | * 1/1999 | Peterson et al. | 424/65 |
| 6,096,299 A | * 8/2000 | Guarracino et al. | 424/76.1 |
| 6,203,810 B1 | * 3/2001 | Alemany et al. | 424/404 |
| 6,245,693 B1 | * 6/2001 | Gagliardi et al. | 442/76 |

\* cited by examiner

*Primary Examiner*—Cathy Lam
(74) *Attorney, Agent, or Firm*—Ohlandt, Greeley, Ruggerio & Perle, L.L.P.

(57) ABSTRACT

One or more particulate active agents are fused to the surface of a substrate web by mixing the particulate agents with a particulate binder having a particle size not exceeding an average diameter of approximately 40 microns and coating the composite mixture onto the surface of the substrate. Thereafter; the coated substrate is heated to a temperature equal to or greater than the Vicat softening temperature of the binder and compressed within the nip of a pair of pressure rolls to achieve fusion. If desired, a top layer may be placed upon the coated composite prior to the compression step. Also disclosed are various products manufactured by the process.

15 Claims, 1 Drawing Sheet

CONTINUOUS SOLID STATE WEB COATING PROCESS AND WEBS PRODUCED THEREBY

This is a Continuation-in-Part of U.S. patent application, Ser. No. 08/903,395, filed on Jul. 22, 1997, now U.S. Pat. No. 6,677,588 which is a Divisional of U.S. patent application, Ser. No. 08/813,055, filed on Mar. 7, 1997 now U.S. Pat. No. 5,792,513. This invention relates to a novel method for the continuous production of a web coated with a layer of a chemically treated, high porosity powdered active substance which is capable of microporous filtration. The active substance is caused to adhere to the web by means of a thermoplastic binder present in a sufficiently small volume that it does not interfere with the adsorbent or otherwise desirable characteristics of the active material, whereas the chemical treatment of the powdered active substance is capable of imparting bacteria control properties to the fluid passing through the thus treated web.

Figure 2:
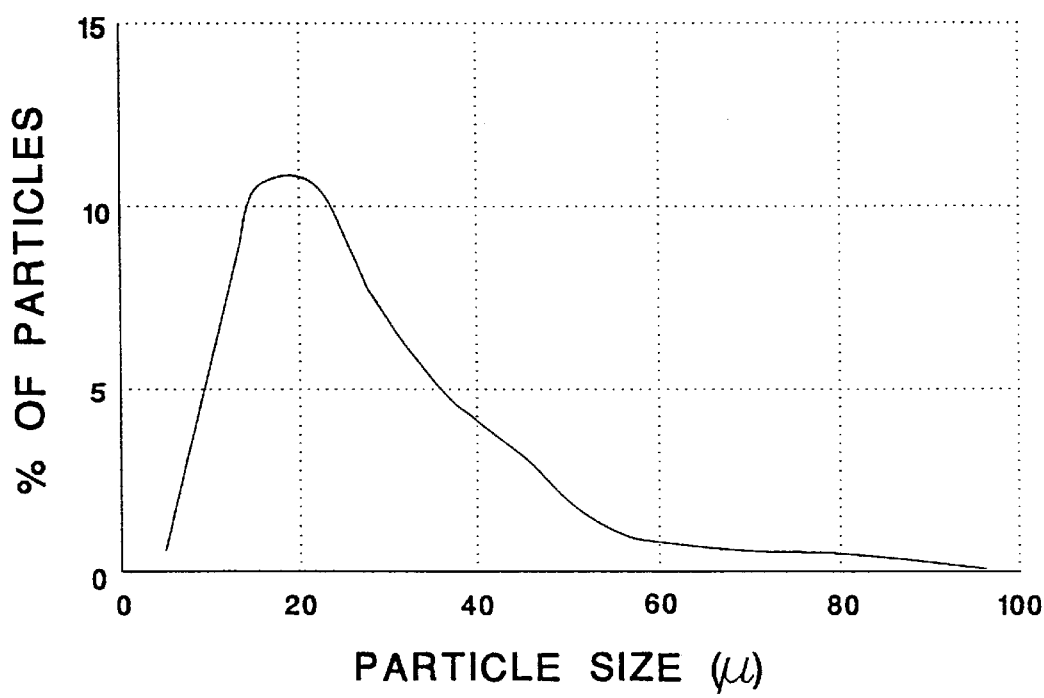

BACKGROUND OF THE INVENTION

The closest known processes to that of this invention are described in Koslow U.S. Pat. Nos. 5,019,311; 5,147,722; 5,189,092; 5,249,948; and 5,331,037, their parent applications, their corresponding foreign patent applications and patents, and the references cited therein.

The above-mentioned patents disclose processes for the production of composite materials which are characterized by primary particles interconnected by a binder material. Some of these processes require high pressure and shear or extrusion through a die with carefully controlled back pressure. These prior art processes are extremely useful in producing a wide variety of articles including extruded solid forms such as activated carbon filters.

It would often be desirable to impregnate, cover, or otherwise treat a relatively fragile web base material with an active component such as a powdered adsorbent or absorbent material. One example would be a nonwoven medium coated with agents having water absorption and odor adsorption characteristics as in a diaper or hygiene products. A number of other related products will be apparent to those skilled in the art such as, for example, coated paper tissues and toweling, and fabrics such as surgical bandages and sanitary napkins. However, the fragile nature of the underlying base material would make it impractical to employ the known prior art techniques which require high pressure and shear.

In the prior art referred to above, the powdered active material is formed into a self-supporting structure by fusion of a thermoplastic material with which it is intimately mixed. However; the pressures, temperatures, and shear involved, or the process equipment used would not permit their application to fragile substrates such as the webs described herein. Accordingly, it is a primary object of the present invention to provide a method for continuously coating a relatively fragile web with a dry mixture of at least one particulate active material and a very finely divided particulate thermoplastic binder.

Another problem associated with using powdered active material is that the porosity does not adequately filter out bacteria and the like. Accordingly, it is an object of the present invention to provide a microporous properties to the treated web by using high porosity particulates having a particle size of between about 5–30 microns, that have an open packing characterization, whereby the coated web exhibits microporous filtration properties. Also, the present invention can include chemical treatment of either the active particles, binder particles or web itself in order to control or kill bacteria.

Other objects, features, and advantages will become apparent from the following description and appended claims.

SUMMARY OF THE INVENTION

In accordance with the present invention a loose, dry composite powder is formed which comprises at least one group of particles of an active ingredient and particles of a thermoplastic binder. The particle size of both the binder particles and the active ingredient, e.g., diatomaceous earth or perlite, is preferably in the range between about 5 to 30 microns so has to impart microporous filtration properties to the web upon which they are coated. The small size of the particles typically cause a mean flow path (MFP) of between about 4 to 6 microns when the mean particle size of the particulates is, for example, 16 microns. Thus, when a web coated with such small particles is spiral wound having, for example, 12 layers of such a coated web, a MFP of 0.7 microns can be achieved. Using these reduced size particulates as the coating of the web converts a relatively inexpensive open-porosity nonwoven web into a high performance material used capable of microfiltration. The active and binder particles, or optionally, the web itself, may be treated with a chemical coating which is capable of imparting properties which are capable of controlling or killing bacteria. The chemical treatment may include quaternary amines, milk protein, triclosan, silver impregnated zeolite or activated carbon. Such factory made precoats provide more uniformity in manufacture, greater flexibility, reduced cracking, pleatability and substantially reduced start-up costs. This chemical treatment provides micro-biological interception using protein solutions which may be applied to the particulates that would then be applied by wet or dry means to a substrate.

The mixture of active and binder powders is applied to the surface of a moving web by means of a knurled roller. The coated web, which can be preheated through a convective or infra-red oven, is then passed through the nip of a pair of rollers, one of which is heated, which apply both heat and pressure to fuse the thermoplastic binder to the active particles and to the underlying web. This step may also be employed to incorporate a second web to achieve a sandwich effect with the active material incorporated between two web surfaces. Upon leaving the heated rollers, the thermoplastic binder sets to form a single, composite structure.

BRIEF DESCRIPTION OF THE DRAWINGS

FIG. 1 is a schematic diagram illustrating an apparatus for the practice of the method of this invention; and FIG. 2 is a graph showing the typical particle size distribution of a binder usable in this invention.

DESCRIPTION OF THE PREFERRED EMBODIMENTS

As has been described above, any of a large number of active particulate agents may be applied to an underlying web in accordance with this invention. Essentially the only limitation relates to the activity desired, e.g. liquid absorption, odor adsorption, medicament delivery, etc. The critical features of this invention, however, reside in the thermoplastic binder which is employed to coalesce the active particles and adhere them to the underlying web. For this purpose, the thermoplastic binder must be in the form of very small particles and must be present in a small enough volume that they do not interfere with the functioning of the active agent. Preferably, the binder will have an effective diameter of not more than 40 microns on average with an optimum size of 20 microns on average. A binder which is suitable for the process of this invention may be produced from normally solid, synthetic organic polymeric thermoplastic resins by the method disclosed in U.S. Pat. No. 3,432,483 of Peoples, et al. Examples of suitable binders are Microthene® F, microfine polyolefin powders produced by Quantum Chemical Company, such as, for example, their low density polyethylene designated FN-510 and their ethylene-vinyl acetate copolymer designated FE-532. FIG. 2 illustrates the typical particle size distribution of Microthene FN-510 powder.

Figure 1:
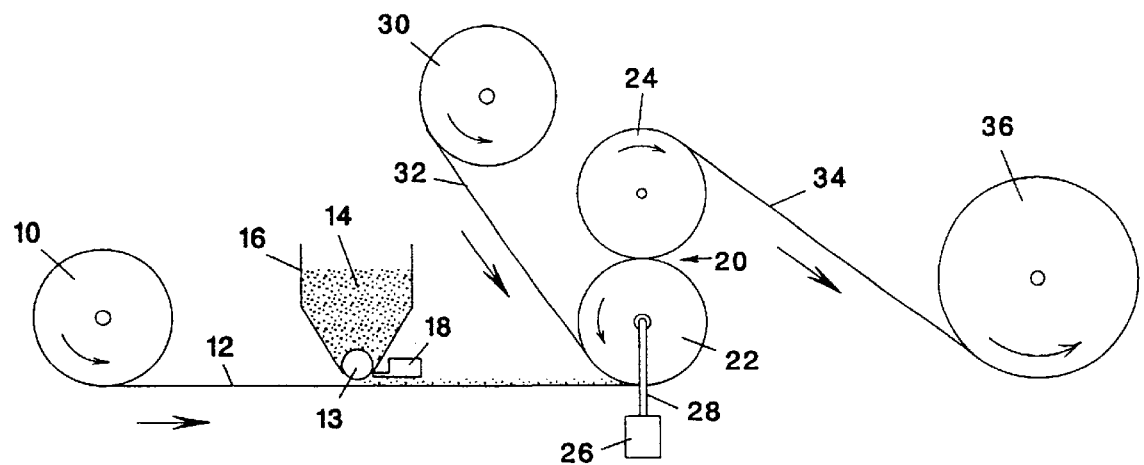

FIG. 1 illustrates an exemplary apparatus for the practice of this invention. A supply roll 10 provides a web 12 of the substrate to be treated, such as a nonwoven tissue or towelling paper. Downstream from supply roll 10 is a knurled roller 13 positioned to receive the composite powder 14 of this invention from a hopper 16 and apply the powder to the upper surface of the web 12. The surface of the knurled roller 13 may be designed to provide a substantially continuous coating or; alternatively, a coating of a specific design such as, for example, stripes on the web surface. A brush 18 may be employed to aid in removing the composite powder from the knurled roller 13. Thereafter, the web 12 is passed through the nip 20 between a heated idler roller 22 and a drive roller 24. A pneumatic cylinder 26 is connected via a rod 28 to the axle of the idler roller 22 to maintain a desired pressure on the web within the nip 20. In passing over the surface of the heated roller 22, the binder is heated to a temperature equal to or greater than its Vicat softening temperature as it enters the nip 20. Within this nip the binder material fuses under pressure with the active material and with the material of the web. In the illustrated apparatus there is provided a second supply roll 30 of a web 32 which may be of the same or a different material from that of base web 12. This web is also passed between the nip 20 of the rollers 22, 24 and on the top of the particulate material which is being fused. Accordingly, the web 34 which leaves the roller 24 is a composite with both a top and bottom sheet, film, or nonwoven layer. Upon leaving the nip 20, the binder cools and hardens, thereby forming the desired composite. The composite web 34 passes onto a takeup roll 36. Some specific examples of the process of this invention are as follows.

Note: The Vicat softening temperature is defined by Quantum Chemical Company, Cincinnati, Ohio, as " . . . the temperature at which the finished [thermoplastic] article becomes too soft to withstand stresses and keep its shape. It is the temperature at which a flat-ended needle of 1 mm cross section under a load of 1 kg penetrates 1 mm into a . . . specimen. In the Vicat test, the temperature of the specimen is increased at a uniform rate."

EXAMPLE 1
Iodine Paper

Iodine paper has utility when used, for example, in a filter unit as a germicidal element.

Both the substrate and the upper layer were 23 cm wide webs of 0.8 oz./sq. yd. spun bonded polyester identified as Reemay type 2016. The production apparatus is as generally shown in FIG. 1 and described above.

The powder mixture consisted of 10% by weight ethylene-vinyl acetate copolymer, (FE532 of Quantum Chemical Company, Cincinnati, Ohio) and 90% by weight iodinated ion exchange resin, 47.5% iodine, balance inert, approximately 20–50 mesh particle size (Grade A605 Puradine™ iodinated resin from The Purolite Company, Bala Cynwyd, Pa.).

The webs moved at the rate of 0.6 m/min and the composite powder was laid down in the amount of 0.02–0.07 g/cm$^2$. The heated roller was 10 inches in diameter and heated by hot oil to a temperature of 135° C. The binder reached its Vicat softening temperature of 75–80° C. in the nip. Pressure in the nip was maintained at approximately 70 kg/cm. The product was a composite medium of good strength and porosity containing nearly 85% by weight of iodated resin. The fact that the resin is not dry prior to processing did not have a significant impact on the quality of the product.

EXAMPLE 2
Carbon/Soda Paper

Carbon and sodium-bicarbonate impregnated paper has particular utility as an odor removing component in, for example, an odor adsorbing sheet used in air filtration applications.

The apparatus was substantially identical to that of Example 1. However; the composite powder comprised 17% FE-532. The remaining 83% was 50% 80–325 mesh (500–44$\mu$) activated carbon and 50% 30–40$\mu$ particles of sodium bicarbonate (NaHCO$_3$). The web was run at a speed of 0.6–0.9 m/min and powder was deposited at the rate of 0.015 g/cm$^2$. The heated roller was at a temperature of 138° C. Three impregnated papers having the same widths as in Example 1 were successfully obtained with (i) both the upper and lower substrates consisting of cellulosic tissue, (ii) both the upper and lower substrates consisting of cellulosic towel stock, and (iii) the lower substrate consisting of cellulosic towel stock and the upper substrate layer consisting of cellulosic tissue stock.

EXAMPLE 3
Carbon Air or Liquid Filter Paper

This adsorbent medium has utility in any situation where carbon treatment of either air or liquid is desirable.

The apparatus was similar to that of Example 1. The lower and upper substrates were both spun bonded polypropylene, (Typar grade 135 of Reemay Corporation). The powder mixture was 30% by weight FE-532 and 70% coconut carbon, of 80–325 mesh (500–44$\mu$). The heated drum was at a temperature of 150° C. and the web speed was 0.6–1.0 m/min. The composite powder was deposited in the amount of 0.015 g/cm$^2$. This adsorbent medium was suitable for air filtration. The process was repeated substituting a bituminous coal based carbon for the coconut carbon. The resulting composite medium was optimal for water filtration applications. Both materials were entirely stable when operated in water and did not release fines.

EXAMPLE 4
Manganese Oxide Paper

This paper has utility as a filter for removal of heavy metals, such as lead.

The apparatus was substantially identical to that of the preceding examples. Both the lower substrate and the upper layer comprised 25 cm wide Castle® facing spun bonded polypropylene from Kimberly-Clark Corporation. The powder mixture was 17% FE-532 and 83% MnO$_2$ of average particle size approximately 44$\mu$. Web speed was 0.8–1.5 m/min. Powder lay-down was 0.015 g/cm$^2$ and the heated drum temperature was 135° C. The resulting composite medium retains the manganese dioxide in its fully active state where it is capable of oxidizing and precipitating lead, cadmium and other heavy metals.

EXAMPLE 5
Super-Absorbent Composite

This product has utility in absorbing liquids and might be used, for example, in diapers.

The apparatus was similar to those described in the preceding examples. Both the lower substrate and the upper layer comprised spun bonded polypropylene from Kimberly-Clark Corporation. The powder mixture was 10% FE-532 and 90% FavorSorb® 880 (a super absorbent acrylic-based polymer obtained from Stockhausen Corporation, Greensboro, N.C. Two runs were made as follows, with production of suitable, super-absorbent composites:

(a) The composite powder laydown was 0.015 g/cm$^2$. Web speed was 0.8 m/min, the temperature of the heated drum was 138° C., and pressure was approximately 100 psi.

(b) The composite powder laydown was 0.36 g/cm$^2$. Web speed was 0.5–0.6 m/min, the temperature of the heated drum was 177° C., and pressure was approximately 100 psi.

This produced a composite medium having excellent water absorption characteristics.

It is believed that the many advantages of this invention will now be apparent to those skilled in the art. It will also be apparent that a number of variations and modifications may be made therein without departing from its spirit and scope. Accordingly, the foregoing description is to be construed as illustrative only, rather than limiting. This invention is limited only by the scope of the following claims.

What is claimed is:

1. A first substrate web having a first surface upon which is deposited a particulate iodinated resin and particles of a thermoplastic binder fused to both of said particulate resin and said first surface, wherein at least one of said substrate, said particulate iodinated resin, and said particles of a thermoplastic binder is treated with an antibacterial agent.

2. The web of claim 1 comprising, in addition, a second substrate web having a second surface spaced from said first substrate web and fused to said thermoplastic binder.

3. The substrate web of claim 1, wherein said antibacterial agent is selected from the group consisting of: a quaternary amine, a milk protein, triclosan, a silver impregnated zeolite, activated carbon, and mixtures thereof.

4. A composite structure comprising a first substrate having a first surface upon which is deposited particulate carbon and particles of a thermoplastic binder fused to both of said particulate carbon and said first surface, wherein at least one of said substrate, said particulate carbon, and said particles of a thermoplastic binder is treated with an antibacterial agent.

5. The web of claim 4 comprising, in addition, a second substrate web having a second surface spaced from said first surface and fused to said thermoplastic binder.

6. The composite structure of claim 4, wherein said antibacterial agent is selected from the group consisting of: a quaternary amine, a milk protein, triclosan, a silver impregnated zeolite, activated carbon, and mixtures thereof.

7. A first substrate web having a first surface upon which is deposited particulate sodium bicarbonate and particles of a thermoplastic binder fused to both of said particulate sodium bicarbonate and said first surface, wherein at least one of said substrate, said particulate sodium bicarbonate, and said particles of a thermoplastic binder is treated with an antibacterial agent.

8. The web of claim 7 comprising, in addition, a second substrate web having a second surface spaced from said first surface and fused to said thermoplastic binder.

9. The substrate web of claim 7, wherein said antibacterial agent is selected from the group consisting of: a quaternary amine, a milk protein, triclosan, a silver impregnated zeolite, activated carbon, and mixtures thereof.

10. A first substrate web having a first surface upon which is deposited particulate manganese oxide and particles of a thermoplastic binder fused to both of said particulate manganese oxide and said first surface, wherein at least one of said substrate, said particulate manganese oxide, and said particles of a thermoplastic binder is treated with an antibacterial agent.

11. The web of claim 10 comprising, in addition, a second substrate web having a second surface spaced from said first surface and fused to said thermoplastic binder.

12. The substrate web of claim 10, wherein said antibacterial agent is selected from the group consisting of: a quaternary amine, a milk protein, triclosan, a silver impregnated zeolite, activated carbon, and mixtures thereof.

13. A composite structure comprising a first substrate having a first surface upon which is deposited a particulate liquid absorbent and particles of a thermoplastic binder fused to both said particulate liquid absorbent and said first surface, wherein at least one of said substrate, said particulate liquid absorbent, and said particles of a thermoplastic binder is treated with an antibacterial agent.

14. The web of claim 13 comprising, in addition, a second substrate web having a second surface spaced from said first surface and fused to said thermoplastic binder.

15. The composite structure of claim 13, wherein said antibacterial agent is selected from the group consisting of: a quaternary amine, a milk protein, triclosan, a silver impregnated zeolite, activated carbon, and mixtures thereof.

* * * * *